(12) United States Patent
Guit et al.

(10) Patent No.: US 6,353,100 B1
(45) Date of Patent: Mar. 5, 2002

(54) PROCESS FOR THE PREPARATION OF ε-CAPROLACTAM

(75) Inventors: Rudolf P. M. Guit, Maastricht; Wim Buijs, Schinnen, both of (NL)

(73) Assignees: DSM N.V., Heerlen (NL); Du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/260,143

(22) Filed: Mar. 1, 1999

Related U.S. Application Data

(63) Continuation of application No. PCT/NL97/00488, filed on Aug. 28, 1997.
(60) Provisional application No. 60/027,496, filed on Sep. 30, 1996.

(30) Foreign Application Priority Data

Sep. 2, 1996 (EP) .............................. 96202438

(51) Int. Cl.[7] ...................... C07D 201/00; C07D 201/08
(52) U.S. Cl. ...................................................... 540/538
(58) Field of Search ......................................... 540/538

(56) References Cited

U.S. PATENT DOCUMENTS

| | | | |
|---|---|---|---|
| 3,485,821 A | 12/1969 | Sheehan | 260/239.3 |
| 4,730,040 A | 3/1988 | Vagt et al. | 540/538 |
| 4,730,041 A | 3/1988 | Hutmacher et al. | 540/538 |
| 4,731,445 A | 3/1988 | Hutmacher et al. | 540/538 |
| 4,963,672 A | 10/1990 | Merger et al. | 540/538 |
| 5,068,398 A | 11/1991 | Merger et al. | 560/156 |
| 5,700,934 A | * 12/1997 | Wolters et al. | 540/538 |
| 5,717,089 A | * 2/1998 | Wolters et al. | 540/538 |
| 5,780,623 A | * 7/1998 | Guit et al. | 540/538 |

FOREIGN PATENT DOCUMENTS

| | | | |
|---|---|---|---|
| DE | 1795013 | | 4/1972 |
| DE | 3602375 A1 | | 7/1987 |
| DE | 3602376 A1 | | 7/1987 |
| DE | 3602377 A1 | | 7/1987 |
| DE | 3843791 A1 | | 7/1990 |
| EP | 0234295 A2 | | 9/1987 |
| EP | 0242505 | | 10/1987 |
| EP | 729 943 | * | 9/1996 |
| EP | 729 944 | * | 9/1996 |

* cited by examiner

*Primary Examiner*—Bruck Kifle
(74) *Attorney, Agent, or Firm*—Pillsbury Madison & Sutro LLP

(57) ABSTRACT

Process for the preparation of ε-caprolactam, in which in a step (a) a compound with the general formula:

$$O=CH-(CH_2)_4-C(O)-R \quad (1)$$

Figure 1:
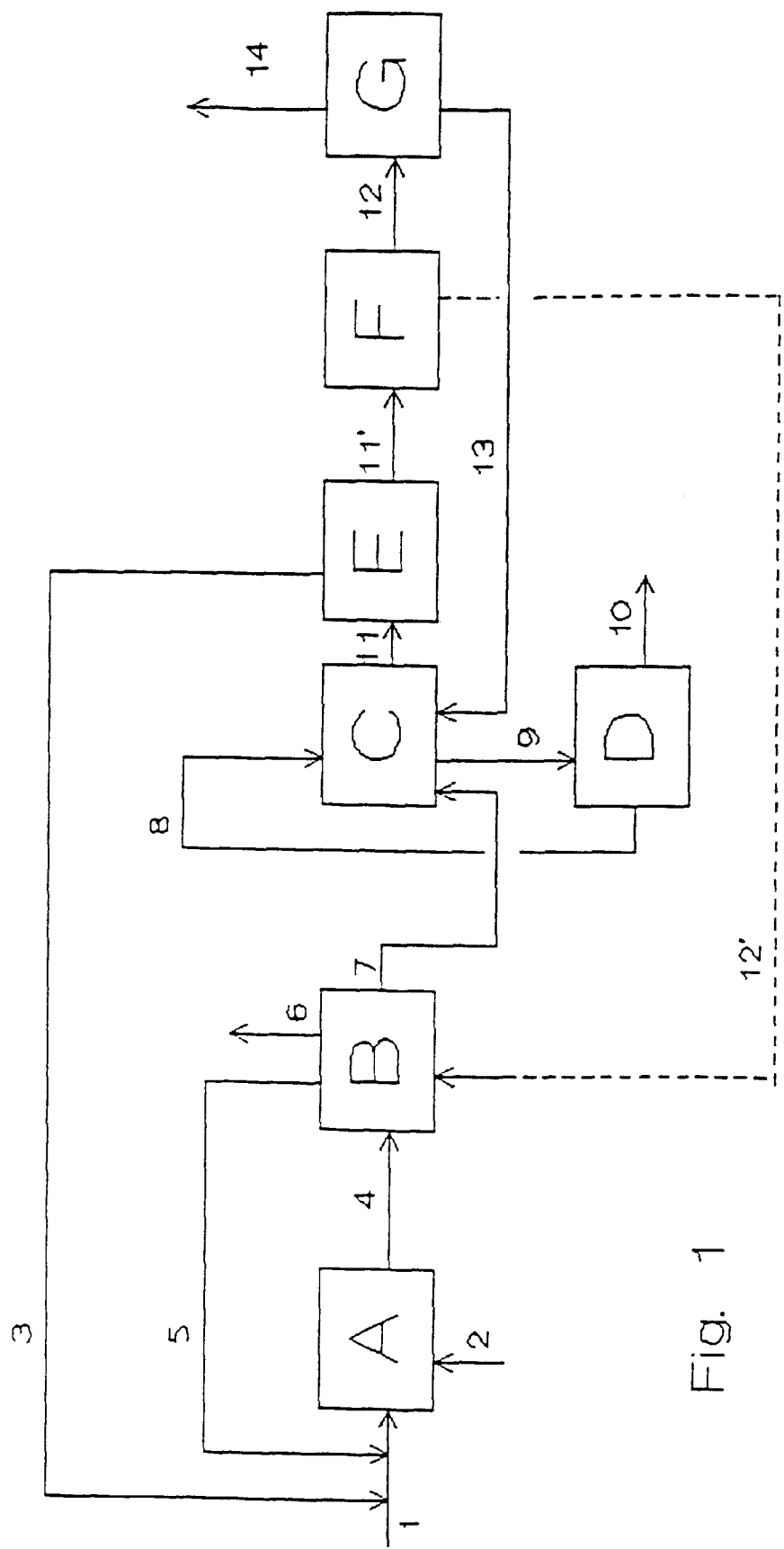

in which R is —OH, —NH$_2$ or O—R', in which R' is an organic group with 1 to 10 carbon atoms, is contacted with ammonia and hydrogen in a suitable solvent at elevated pressure in the presence of a hydrogenation catalyst to a mixture of primary amino compounds and ε-caprolactam, followed by a separate second step (b) in which the primary amino compounds are reacted to ε-caprolactam, wherein the solvent in step (a) is an aqueous medium, including water, the yield to ε-caprolactam in step (a) is more than 10%, calculated on the initial molar amount of the compound according to formula (1), that ε-caprolactam is separated from the aqueous mixture obtained in step (a) by extraction and that the aqueous mixture resulting from the extraction, containing the primary amino compounds, is used in step (b).

13 Claims, 1 Drawing Sheet

PROCESS FOR THE PREPARATION OF ε-CAPROLACTAM

This application claims the benefit of U.S. Provisional Application No. 60/027,496, filed Sep. 30, 1996.

This is a continuation of International application No. PCT/NL97/00488, filed Aug. 28, 1997.

The invention relates to a process for the preparation of ε-caprolactam, in which, in a first step (a), a compound having the general formula:

O=CH—(CH$_2$)$_4$—C(O)—R    (1)

wherein R represents —OH, —NH$_2$ or —OR', and wherein R' represents an organic group with from 1 to 10 carbon atoms, is brought into contact with ammonia and hydrogen in a suitable solvent at elevated pressure and in the presence of a hydrogenation catalyst, to form a mixture of primary amino compounds and ε-caprolactam. This is then followed by a separate second step (b) in which the primary amino compounds are reacted to form ε-caprolactam.

Such a process is described in U.S. Pat. No. 4,730,041. This patent describes a process in which methyl 5-formylvalerate is first reacted with excess ammonia and hydrogen in the pressence of methanol as solvent, and in the presence of a catalyst, such as Raney-nickel, in the liquid phase at 80° C. to yield a mixture of about 89% methyl 6-aminocaproate and about 3% ε-caprolactam. This mixture is subsequently heated to 225° C. to yield 78% ε-caprolactam. The total concentration of all of the reactants in the different process steps was about 10 wt %.

A disadvantage of the process described in this U.S. Pat. No. 4,730,041 is that relatively large-sized process equipment for the (step (b)) cyclization section is required. This is due to the low concentration of reactants in that step. According to the patent the cyclization is also performed at super atmospheric pressures, requiring special process equipment. From an economical/investment point of view, smaller-sized, less expensive, process equipment is generally desired. However, merely using smaller-sized process equipment (which might otherwise seem possible simply by increasing the reactant concentration in the cyclization step) is disadvantageous since a loss of yield is to be expected due to the increased formation of oligomers. See discussion in the article by Mares and Sheehan in Ind. Eng. Chem. Process Des. Dev., Vol. 17, No. 1, 1978, 9–16

The principal object of this invention is to provide a process which can be effectively operated in process equipment of a smaller volume for the cyclization section (step b) as compared to processes of the current state of the art.

This object is achieved by employing the combination of conditions wherein the solvent used in step (a) is an aqueous medium, including water, and the ε-caprolactam yield obtained in step (a) is brought to at least 10%, calculated on the initial molar amount of the compound according to formula (1), and that the ε-caprolactam is separated from the aqueous mixture obtained from step (a) by extraction using an organic extraction agent, and with the aqueous mixture resulting from the extraction step, containing the primary amino compound, is then used as the feed into step (b).

The above results in the following process according to the invention preparing for ε-caprolactam, wherein, in a first step (a), a compound having the general formula:

O=CH—(CH$_2$)$_4$—C(O)—R    (1)

wherein R is —OH, —NH$_2$ or O—R', and wherein R' is an organic group with 1 to 10 carbon atoms, and in an aqueous medium as solvent, is contacted at an elevated pressure with ammonia and hydrogen in the presence of a hydrogenation catalyst to form a mixture of ε-caprolactam and primary amino compounds, and wherein the yield to ε-caprolactam in step (a) is carried to a level of at least 10 molar%, calculated on the initial molar amount of said compound, and extracting ε-caprolactam from said aqueous mixture obtained from step (a) with an organic extraction agent to form an organic extractant solution of ε-caprolactam and a separate residual aqueous mixture, followed by a separate second step (b) wherein said primary amino compounds in said residual aqueous mixture are further reacted to form ε-caprolactam.

By using an aqueous medium (including water) as the solvent in step (a) and by increasing the ε-caprolactam yield in step (a), ε-caprolactam can be advantageously separated from the reaction mixture prior to step (b) by extraction. Then, as a result of the separation of the ε-caprolactam prior to step (b), a smaller-sized volume of process equipment can be effectively used in step (b) while avoiding the drawbacks of the present state of the art.

A further advantage of the present invention is that a substantial part of the ε-caprolactam can be prepared at the relatively low temperature used in the first step (a). By contrast, in the process of U.S. Pat. No. 4,730,041, almost all of the ε-caprolactam is prepared in the second step (b) at relatively high temperatures, for example 300° C. This is a significant temperature difference. By operating according to the present invention, the overall consumption of energy required to prepare one mol of ε-caprolactam of the process will be less than that of the present state of the art process.

Further, the fact that less ε-caprolactam is exposed to the higher temperature of the second step is also advantageous in that the level of impurities in the ε-caprolactam obtained is lowered. Moreover, at higher temperatures ε-caprolactam tends to react more readily to impurities than at lower temperature levels.

Another advantage of the present invention is that ε-caprolactam can be obtained in higher overall yields than was possible with the state of the art process as described in U.S. Pat. No. 4,730,041.

Examples of processes which yield more than 10% of ε-caprolactam in a process comparable to step (a) are generally not reported in the prior art, probably because at such higher yields ε-caprolactam oligomers can be formed. Oligomer formation is as a rule considered to be disadvantageous when the desired product is ε-caprolactam. However, we have now found that such oligomer formation in step (a) does not have to result in a reduction of the overall ε-caprolactam yield.

It has further been found that ε-caprolactam can be exclusively separated from an aqueous mixture containing 6-aminocaproic acid, 6-aminocaproamide and/or their respective oligomers. These primary amino compounds are the most important reaction products of step (a) and are the starting compounds for the further reaction to ε-caprolactam in step (b).

The extraction of ε-caprolactam from the aqueous mixture can be performed with any organic extraction solvent which is substantially immiscible with the aqueous mixture. By substantially immiscible is here meant that the mixture of organic extraction solvent and the aqueous mixture results in two segregated phases at the extraction temperature. Preferable the mutual solubility under the conditions of the extraction is not higher than 30 wt. % and more preferably less than 20 wt. %.

Examples of such solvents include ethers, for example methyl tert-butylether, aromatics, for example toluene, benzene and xylene and parafinic solvents, for example decaline. Preferably chlorinated hydrocarbons with 1 to 10 carbon atoms are used. Examples are dichloromethane, chloroform or 1,1,1-trichloroethane.

Examples of another class of extraction agents are phenol and alkyl phenols. A preferred class of alkyl phenols are those which have a boiling point higher than that of ϵ-caprolactam. Preferably, the alkyl phenol has a boiling point higher than the boiling point of ϵ-caprolactam, which is 270° C. at 0.1 MPa. Alkyl phenols have high boiling points at atmospheric pressure. Therefore, in this context, the boiling points are advantageously compared at reduced pressures of, for example, 1.3 kPa (10 mmHg). Caprolactam has a boiling point of 140° C. at 10 mmHg, while dodecyl phenol, for example, has a boiling point of 190° C. at that pressure. By preference, the boiling point of the alkyl phenol is at least about 5° C., and in particular, at least about 15° C. above the boiling point for caprolactam at 1.3 kPa (10 mmHg). The upper limit for the boiling point of the alkyl phenol is about 400° C. at 10 mmHg. Preferably, the alkyl phenol is chosen so as not to form an azeotropic mixture with ϵ-caprolactam.

The alkyl phenol is phenol substituted with one or more alkyl groups. The total number of carbon atoms of the alkyl group(s) is preferably between 6–25 and more preferably between 8–15. Examples of specific alkyl phenolic compounds include dodecyl phenol, octyl phenol, nonyl phenol, n-hexyl phenol, 2,4-diisobutyl phenol, 2-methyl-4,6-di-tert-butyl phenol, 3-ethyl-4,6-di-tert-butyl phenol, 2,4,6-tri-tert-butyl phenol, and mixtures of any thereof. U.S. Pat. No. 4,013,640 discloses additional alkyl phenols which may also be used, the complete disclosure thereof is hereby incorporated by reference. Other mixtures of alkyl phenols can also be used.

Most preferred extraction solvents are aliphatic or cycloaliphatic compounds having one or more hydroxyl groups. Such alcohol compounds have preferably 4–12 carbon atoms and more preferably 5–8 carbon atoms. Preferably one or two and more preferably only one hydroxyl group is present. Preferably hindered alcohols are used. A hindered alcohol is a compound in which the hydroxyl group is bonded to a —$CR^1R^2R^3$ in which $R^1$ and $R^2$ are alkyl groups and $R^3$ is an alkyl group or hydrogen. This is advantageous in a process in which the resulting aqueous phase are used as feed to prepare ϵ-caprolactam. Hindered alcohols are less susceptible to react to N-alkylation products of ϵ-caprolactam.

Examples of compounds having two hydroxyl groups are hexanediol, nonanediol, neopentylglycol, methyl-methylpropanediol, ethyl-methylpropanediol or butyl-methylpropanediol. Examples of compounds having one hydroxyl group are cyclohexanol, n-butanol, n-pentanol, 2-pentanol, n-hexanol, 4-methyl-2-pentanol, 2-ethyl-1-hexanol, 2-propyl-1-heptanol, n-octanol, iso-nonylalcohol, n-decylalcohol and mixtures of linear and branched $C_8$-alcohols, mixtures of linear and branched $C_9$-alcohols and mixtures of linear and branched $C_{10}$-alcohols. Mixtures of the above mentioned alcohols can also be used. Preferred alcohols have a high affinity for ϵ-caprolactam, a lower boiling point than ϵ-caprolactam, a large density difference with water, commercially available, low mutual solubility with water and/or are biodegradable.

The extraction step is carried out at a temperature which is above the melting point of the organic extraction agent. The temperature of extraction can be generally between room temperature and about 200° C.

The extraction step is carried out under a reduced pressure, but the actual pressure used is not critical. The pressure during the extraction step can be, for example, between about 0.1 MPa and about 2.0 MPa, and preferably, between about 0.1 MPa and about 0.5 MPa. The extraction step can be carried out in well known extraction apparatus, for example a counter current column or a series of mixer/settlers.

The extraction step yields an organic phase which, in general, may contain up to about 50 wt. % ϵ-caprolactam, along with between about 0 and about 15 wt. % water.

The starting compound according to formula (1) (the aldehyde compound) can itself be obtained by hydroformylation of the corresponding pentenoate ester, acid or amide as, for example, described for the ester in WO-A-9426688 and WO-A-9518089, and for the acid in, for example, WO-A-9518783, the disclosures of which are incorporated herein by reference. Preference is given to the 5-formylvalerate ester as the starting compound because this compound is at present more easily obtainable.

In formula (1), R is defined as one of the groupings —OH, —$NH_2$ or —O—R', and wherein R' is preferably an organic group with 1 to 20 carbon atoms. This organic group is an alkyl, cycloalkyl, aryl or aralkyl group. More preferably R' is an alkyl group. Examples of R' groups include methyl, ethyl, propyl, isopropyl, n-butyl, tert-butyl, isobutyl, cyclohexyl, benzyl and phenyl. By preference R' is methyl or ethyl.

Step (a) can be performed by the generally known methods for reductive amination. The higher yield to ϵ-caprolactam in step (a) can be achieved by choosing conditions which are generally known to improve product yields. When starting from 5-formylvaleric acid the conditions as described in for example U.S. Pat. No. 4,730,040 can be applied and when starting from a 5-formylvalerate ester the conditions as described in U.S. Pat. No. 4,730,041 can be applied. Ammonia is preferably present at a molar excess with respect to the aldehyde compound. When 5-formylvalerate ester is the starting material, it is preferred to perform step (a) in the presence of an additional alcohol solvent and more preferably in the presence of the corresponding alcohol of the ester (R'—OH). The presence of the alcohol improves the solubility of the 5-formylvalerate ester in the aqueous reaction mixture. The concentration of the alcohol is preferably between about 2 and 20 wt. % and more preferably between about 5 and 15 wt. %. The temperature in step (a) is preferably between about 50 and 150° C. and the pressure is between about 0,5 and 20 MPa.

The hydrogenation catalyst comprises one or more of the metals choosen from the metals of groups 8–10 of the Periodic System of the Elements (New IUPAC notation; Handbook of Chemistry and Physics, 70th edition, CRC Press, 1989–1990) for example nickel, cobalt, ruthenium, platinum or palladium. Preference is given to Ru-, Ni- or Co-containing catalysts. In addition to Ru, Co and/or Ni the catalysts can also contain other metals for example Cu, Fe and/or Cr. The content of these additional metals may, for example, be up to 20 wt. %, based on the total metal content.

The catalytically active metals may optionally be employed on a carrier. Suitable carriers include for example aluminium oxide, silica, titanium oxide, zirconium oxide, magnesium oxide, carbon or graphite. Non-carried metals can also be used. An example of a non-carried metal is finely dispersed ruthenium. Preferred Ni- and Co-containing catalysts are Raney nickel and Raney cobalt optionally in combination with small amounts of another metal, for example Cu, Fe and/or Cr.

Most preferred are ruthenium-containing catalysts. High yields to ϵ-caprolactam in step (a) over a prolonged period of time are possible when using ruthenium-containing catalysts. Examples of possible ruthenium-containing catalysts are non-carried, or unsuported, metal catalysts, for example finely dispersed ruthenium, or ruthenium supported on a carrier, for example ruthenium on a carbon, alumina, graphite or $TiO_2$ carrier.

Step (a) is desireably performed according to the preferred embodiment (described hereinbelow). It has also been found that higher overall yields to $\epsilon$-caprolactam can then be achieved.

In its preferred embodiment, step (a) is performed in two separate substeps: substep (a1) and substep (a2). In substep (a1) the aldehyde compound corresponding to formula (1) is reacted with ammonia under non-hydrogenating conditions and in substep (a2) the reaction product obtained in substep (a1) is converted to $\epsilon$-caprolactam and primary amino compounds under hydrogenating conditions in the presence of ammonia.

Substep (a1) is carried out under non-hydrogenating conditions. The term 'non-hydrogenating conditions' means that the reaction conditions are such that, either no hydrogen is present or, if hydrogen is present, then the aldehyde compound according to formula (1) or a reaction product thereof is not, or is virtually not, reduced by the hydrogen. In general, non-hydrogenating conditions are realized by carrying out the first substep (a1) in the absence of a hydrogenation catalyst.

Variations in technique are possible. In one such embodiment of the present process, the hydrogen (which is needed in substep (a2)) can already be present in substep (a1). On the other hand if the hydrogenation catalyst is already introduced and present in this substep (a1), then non-hydrogenating conditions can nonetheless be achieved by avoiding the addition of hydrogen to the reaction mixture until after completing substep (a1). A third possible embodiment is that both hydrogen and the hydrogenation catalyst are absent from substep (a1).

The temperature in substep (a1) may be up to about 120° C. and is preferably between about 0° C. and 100° C. More preferably the temperature is between about 20–100° C. It has been found that the best results with regard to the overall yield obtained for primary amino compounds and $\epsilon$-caprolactam are achieved when the conversion of the aldehyde compound in substep (a1) is more than 90%, preferably above about 99%. If the conversion is too low, this can result in an increase in the formation of, for example, the 6-hydroxycaproate ester (or acid or amide) and/or secondary amino compounds. Formation of these compounds will then negatively influence the overall process yield to $\epsilon$-caprolactam.

As explained above, too short a contact or residence time in substep (a1) may result in undesirable by-product formation. The optimal residence or contact time at which the conversion of the aldehyde starting compound is virtually completed, will depend on the overall combination of reaction conditions, for example: temperature, concentration of reactants and method of mixing. Longer contact, or residence, times than are needed to achieve the above conversion are, of course, possible. The optimal residence time or contact time can be easily determined by the man skilled in the art.

Starting from the temperature and concentration range herein described, the residence or contact times, under normal mixing conditions, will generally preferably be more than about 5 seconds. Preferably, the residence or contact time will be less than about 2 minutes.

Substep (a1) is carried out in the presence of ammonia, and preferably a molar excess of ammonia is chosen such that the molar ratio ammonia:aldehyde compound is between 1:1 and 500:1 calculated on the starting amount of the aldehyde compound. Preferably this ratio is above about 5:1. If this ratio is too low the $\epsilon$-caprolactam yield is negatively influenced. Preferably the molar ratio ammonia:aldehyde compound (aldehyde compound and its reaction products) in substep (a1) is between about 3:1 and 25:1 more preferably between about 5:1 and 15:1.

Water will be formed in substep (a1) as a reaction product of the reaction between the aldehyde compound and ammonia. Preferably substep (a1), and substep (a2) as well, are performed in the presence of at least 10 weight percent of water. The water content of the reaction mixture in substep (a1) is preferably between about 15–60 wt. % and more preferably between about 20–50 wt. %.

The concentration of the aldehyde compound, or more accurately, the concentration of the sum of aldehyde compound and its reaction products in step (a) or in substep (a1) is generally between about 1 and 50 wt. % and preferably between about 10 and 35 wt. %. High yields to $\epsilon$-caprolactam can be advantageously achieved at these higher concentrations.

The pressure in substep (a1) is not critical. The pressure is generally equal or greater than the resulting equilibrium pressure of the liquid reaction mixture and the temperature employed.

Substep (a1) can be carried out in the presence of a catalyst, for example an acid ion exchanger or an acidic metal oxide catalyst, for example alumina or $TiO_2$. Still, the conversion of the aldehyde starting compound in the first step also proceeds favorably in the absence of a catalyst. Because the overall yield to $\epsilon$-caprolactam is not greatly influenced by the presence of a catalyst in the first step, such a catalyst is generally not used.

The process according to the invention can be performed batch wise or continuously. A large scale commercial process will preferably be performed continuously. For substep (a1), it is important that the reactants are sufficiently contacted at a certain temperature during a specified period of time optionally in the presence of a catalyst as described above. Any manner of contacting will usually suffice. For example a tube reactor with or without internal baffling or packing or a static mixer is a possible contacting unit for substep (a1). To control the temperature in substep (a1) it may be advantageous to use cooling devices, for example cooled walls or a cooling spiral placed in the contacting unit.

The above described ratios and concentrations and their preferred values for substep (a1) also apply for substep (a2) unless otherwise mentioned. Moreover the composition of the aqueous reaction mixture obtained in substep (a1) is by preference, directly and without substantial separation of any of the compounds of the mixture, used in substep (a2). This is advantageous because it results in a more simple process.

The reaction product obtained from substep (a1) is converted in substep (a2) to $\epsilon$-caprolactam and the primary amino compounds under hydrogenating conditions in the presence of ammonia.

The primary amino compounds so obtained include 6-aminocaproamide, 6-aminocaproate ester and 6-aminocaproic acid. Oligomers which may be formed in step(a) can, in this invention, also be considered as primary amino compounds and as precursors to $\epsilon$-caprolactam. The oligomers are for the greater part dimers of 6-aminocaproic acid or dimers of 6-aminocaproamide. Trimers and higher oligomers may also be formed.

When the aldehyde compound according to formula (1) is a 5-formylvalerate ester a mixture of $\epsilon$-caprolactam, 6-aminocaproic acid, 6-aminocaproamide and none or a small amount of 6-aminocaproate ester and/or oligomers will be obtained in substep (a2). The hydrolysis of the ester-group mainly takes place in substep (a2). When the aldehyde compound is 5-formylvaleric acid a mixture of ε-caprolactam, 6-aminocaproic acid, possibly some 6-aminocaproamide and possibly some oligomers will be obtained in substep (a2).

By 'hydrogenating conditions' it is understood in this invention that the reaction conditions are such that the intermediate reaction product(s) obtained in substep (a1) can be reduced by hydrogen. In general hydrogenation conditions are achieved when hydrogen and a hydrogenation catalyst are present. The hydrogenation catalyst has been described above.

The total pressure used in substep (a2) is generally between 0.5 and 20 MPa. The pressure is preferably between 0.5–10 MPa and more preferably between 1–5 MPa.

Substep (a2) is in general carried out at a temperature higher than about 40° C. In general the temperature will be lower than about 200° C. To achieve optimal overall yields to ε-caprolactam the temperature is more preferably between about 70 and 180° C. Most preferably the temperature is above about 100° C. because high yields to ε-caprolactam can be obtained.

The residence or contact time in substep (a2) should be sufficiently long so as to reduce virtually all the intermediate products formed in substep (a1) to the desired yield of ε-caprolactam and primary amino compounds. Operative residence or contact times are preferably between around about a half minute up to about a couple of hours. When the process is carried out batch-wise or in a continuously operated slurry reactor the contact or residence time respectively will generally be higher than the residence time when a continuously operated tube reactor is used.

Substep (a2) may be performed continuously in a fixed bed reactor in which the heterogeneous hydrogenation catalyst is present. An advantage of this reactor is that the reactants are easily separated from the hydrogenation catalyst. Another mode of operating substep (a2) is by use of one or more continuously operated contactors in series in which the hydrogenation catalyst is present as a well mixed slurry (slurry reactor). This manner of operation has the advantage that the heat of the reaction from substep (a2) can be easily controlled by, for example, a cooled feed or by way of internally placed cooling devices. Examples of specific and suitable slurry reactors are single or multiple-staged bubble columns or a gas lift-loop reactor or a continuously stirred tank reactor (CSTR). The slurry-hydrogenation catalyst can be separated from the reaction mixture after substep (a2) by, for example, using hydrocyclones and/or by filtration, for example by cake- or cross-flow filtration.

The catalyst concentration in substep (a2) may be choosen over a wide range. In a fixed bed reactor the amount of catalyst per volume will be high while in a slurry reactor this concentration will in general be lower. In a continuously-operated slurry reactor the weight fraction of catalyst (including the carrier) is typically between 0.1 and 30 weight % relative to the total content of the reactor. The weight fraction will for example depend on the use of a carrier and the kind of carrier.

The yield to ε-caprolactam in step(a) is in the process according to the invention above 10 wt. % and preferably higher than 20 wt. %.

The high yields to ε-caprolactam can be achieved by, for example, increasing the concentration of the reactants in substeps (a1) and (a2); increasing the residence time in step (a), or in substep (a2) when performing the two step reductive amination; increasing the temperature in substep (a1); and/or by using a ruthenium containing catalyst in step (a) (or substep (a2)).

Ammonia, hydrogen, the hydrogenation catalyst and the alcohol (if present) are preferably separated from the reaction mixture obtained in the reductive amination step (a) prior to the extraction according to the process of the invention. Hydrogen and part of the ammonia can be advantageously be separated by reducing the pressure and performing a gas/liquid separation. An example of such an operation is a flash operation performed at between ambient pressure and 0.5 MPa. The hydrogen and ammonia can advantageously be recycled to step (a).

In a subsequent step the alcohol (if present) can be separated. It has been found that it is advantageous to perform the cyclization step (b) in the pressence of less than 1 wt % and more preferably less than 0.1 wt % of alcohol. Thus when the resulting mixture from step (a) contains alcohol it is advantageous to separate this compound. It has been found that the presence of alcohol during the cyclization promotes the formation of the corresponding N-alkyl caprolactam, an undesired by-product. The presence of small quantities of these N-alkylated products, for example N-methyl ε-caprolactam, in final ε-caprolactam makes the ε-caprolactam less suitable for use as starting material for nylon-6 fibers. Because these N-alkylated products are difficult to separate from the final ε-caprolactam, it is favorable that they do not form or that their formation is minimized in the process according to the invention.

Separating the alcohol may be performed by any known method known to the man skilled in the art, for example by distillation or stripping, for example by steam stripping.

Step (b) may be performed in the gas phase as described in for example U.S. Pat. Nos. 4,599,199 or in 3,658,810 by contacting a (preferably concentrated) mixture as obtained in step (a) with overheated steam having a temperature between about 150–400° C. at about atmospheric pressure. Such gas phase processes are advantageous because ε-caprolactam is obtained in a gaseous steam phase in which no oligomers are present. Separation of ε-caprolactam and oligomers can thus be avoided.

Preferably step (b) is performed in the liquid phase at super atmospheric pressures such as for example described in the aforementioned U.S. Pat. No. 4,730,040, WO-A-9600722 and in the above mentioned article of Mares and Sheehan. High yields of ε-caprolactam of high quality can be obtained with these liquid phase processes. More preferably step (b) is performed in the liquid phase as discussed below.

The concentration of ammonia in the liquid mixture employed in step (b) is preferably below about 5 wt. % and more preferably below about 3 wt. % and most preferably below about 1 wt. %. Higher concentrations of ammonia have a negative effect on the yield to ε-caprolactam per pass in a continuous process.

The concentration of ε-caprolactam and ε-caprolactam precursors in step (b) is preferably between 5 on 50 wt. % and more preferably between 10–35 wt. %.

The elevated temperature in step (b) is between about 200 and 350° C. Preferably the temperature in step (b) is higher than 290° C. because of higher yield per pass to ε-caprolactam.

The pressure in step (b) is preferably between 5.0 and 20 MPa. Normally this pressure will be greater than or equal to the resulting pressure of the liquid reaction mixture and the temperature employed.

Step (b) can be performed continuously in process equipment resulting in high and low rates of backmixing.

The ε-caprolactam can be separated from the reaction mixture obtained in step (b) by for example crystallization, extraction or by distillation. Preferably ε-caprolactam is separated by extraction in which the same extraction agents and conditions as described before can be applied. More preferably the effluent obtained in step (b) is subjected to the same extraction procedure as is used for the effluent of step (a) as described above. Prior to this extraction step it is prefered to separate part or all of the ammonia present in the aqueous mixture of step (b) in order to prevent a build up of ammonia in the process.

Extraction of ε-caprolactam from the effluent of step (b) is especially advantageous as compared to distillation separation when oligomers are also present in the aqueous mixture containing the ε-caprolactam. When using distillation more oligomers are usually formed and obtained in the residue of the distillation(s) in a high concentration. Because of these high oligomer concentrations and the solidification of the oligomers, fouling of the process equipment can occur, for example, pipes and other components. This disadvantage does not occur when extraction is used as the method for isolating ε-caprolactam.

Another advantage of the extraction procedure over distillation is that the amine compounds which can be present in the effluent of step (b) are not exposed to the high reboiler temperatures of the distillation. These high temperature conditions tend to induce formation of by-products and (more) oligomers. By using extraction as the method for isolating ε-caprolactam the exposure of the ε-caprolactam precursors to the high temperatures of the reboilers can be avoided or at least substantially reduced.

The ε-caprolactam may be purified by methods known for purifying ε-caprolactam obtained by Beckmann rearrangement. An example of a one method for purifying ε-caprolactam is described in U.S. Pat. No. 5,496,941.

A non restrictive example of an embodiment of the process starting from methyl 5-formylvalerate according to the invention is given in FIG. 1. The illustrated process is a schematic representation of the process equipment used in the below examples.

In FIG. 1 a mixture of methyl 5-formylvalerate/water/ammonia/methanol (1) is fed to the reductive amination reactor (A). Also fed to (A) is sufficient hydrogen (2). The effluent from the reductive amination reactor (A) is lead by line to vessel (B) wherein ammonia and methanol is separated by steam stripping. Part of the methanol is recovered via line (6) and the rest is recycled to the reductive amination stage (A) via line (5). The resulting reaction mixture is lead via line (7) to a counter current extraction column (C) and is then extracted with the extraction solvent through (8) to yield a extraction solvent stream (9) rich in ε-caprolactam and an aqueous mixture via line (11) rich in 6-aminocaproic acid, 6-aminocaproamide and oligomers. In vessel (E) water is first separated and removed from the mixture by distillation and recycled to the reductive amination stage via line (3). The resulting now concentrated aqueous mixture is fed via line (11') to the cyclization reactor (F) resulting, in an effluent in line (12) rich in ε-caprolactam, but also containing some unconverted oligomers, plus 6-aminocaproic acid and 6-aminocaproamide. After separating ammonia via line (14), for instance, by steam stripping in vessel (G) the aqueous mixture (13) is recycled to the extraction column (C). Optionally the effluent of vessel (F) may be recycled to the steam stripper (B) via (12'). In this manner the feed to the extraction column (C) is concentrated and ammonia may be effectively separated by using less expensive and complicated process equipment. The ε-caprolactam extraction solvent mixture obtained in column (C) is supplied via line (9) to a separation unit (D) in which the organic solvent is separated from the ε-caprolactam by, for example, distillation, and ε-caprolactam is obtained through line (10). The extraction solvent itself, now poor in ε-caprolactam, is returned via line (8) to column (C). In the various recirculating streams, purges (not shown) will preferably be provided to overcome build up of contaminants and by-products.

The invention will now be elucidated with the following non-restricting examples.

The composition of the resulting mixtures of the experiments are sometimes expressed in mol percentages. The molar percentage of a component is represented by the molar fraction (×100%) of the molar amount of converted methyl 5-formylvalerate (M5FV) which contributes to that specific component. For example if the starting amount of M5FV is 100 mol and the resulting mixture contains 50 mol ε-caprolactam and 25 mol of dimers then the molar contribution to ε-caprolactam will be 50 mol % and the molar contribution to the dimers will be 50 mol % (totaling 100 mol %). When no oligomers such as dimers are present in the mixture the above molar percentages are the same as the molar yield as expressed below:

$$\text{yield of component } x = \frac{\text{mol component } x \text{ formed}}{\text{mol M5FV converted}} * 100\%$$

Extraction Experiments

EXAMPLE I 200 ml of a mixture of 20 wt. % ε-caprolactam and 5 wt. % 6-aminocaproic acid in water was well mixed for a time sufficient to reach equilibrium with 200 ml chloroform at room temperature and atmospheric pressure. The water phase was separated from the chloroform by phase separation. The water phase was again mixed with 200 ml chloroform. as above and separated from the chloroform by phase separation. The two chloroform phases were combined and analyzed by high pressure liquid gaschromatography (HPLC). The water phase was also analyzed and the partition coefficient (calculated as the concentration of ε-caprolactam in the organic chloroform phase divided by the concentration of ε-caprolactam in the aqueous phase at (almost) equilibrium conditions) was 0.74. No detectable amount of 6-aminocaproic acid (<0.01 wt. %) was found in the chloroform phase.

EXAMPLE II

Example I was repeated with dichloromethane. The partition coefficient was 0.84. No detectable amount of 6-aminocaproic acid was found in the dichloromethane phase.

EXAMPLE III

Example I was repeated with methyl tert-butylether. The partition coefficient was 0.1. No detectable amount of 6-aminocaproic acid (<0.01 wt. %) was found in the tert-butylether phase.

EXAMPLE IV

Example I was repeated with a mixture as obtained in a step (a) of the present invention containing 5.08 wt. %

ε-caprolactam, 3.09 wt. % 6-aminocaproic acid, 7.51 wt. % 6-aminocaproamide and 1.99 wt. % oligomers. The partition coefficient for ε-caprolactam was as in Example I. No detectable amounts (<0.01 wt. %) of 6-aminocaproic acid, 6-aminocaproamide or oligomers were found in the organic phase.

EXPERIMENT V

Example IV was repeated at 80° C. using the same volume of dodecylphenol instead of chloroform. The partition coefficient for ε-caprolactam was about 11.

Examples I–V illustrate that ε-caprolactam is successfully separated from aqueous mixtures containing 6-aminocaproic acid, 6-aminocaproamide and/or oligomers.

These batch examples also show that an almost 100% separation of ε-caprolactam is possible in a continuously operated extraction; for example in a counter current extraction column or in a series of mixer/settlers.

EXAMPLE VI 100 g of an aqueous mixture containing 15.5 wt. % ε-caprolactam, 5.2 wt. % 6-aminocaproic acid, 17.4 wt. % 6-aminocaproamide and 2.2 wt. % oligomers of 6-aminocaproic acid and 3.4 wt. % oligomers of 6-aminocaproamide was mixed well, long enough to reach equilibrium, with 100 g of 4-methyl-2-pentanol at 80° C.

The partition coefficient of ε-caprolactam was 3.3. No detectable amounts of 6-aminocaproic acid and oligomers of 6-aminocaproic acid were found in the alcohol phase. The partition coefficient of 6-aminocaproamide was 0.45 and of oligomer of 6-aminocapro-amide was 0.66. By extracting the alcohol phase with fresh water the 6-aminocaproamide and its oligomers could be succesfully separated from the alcohol phase containing the ε-caprolactam product.
Synthesis and Conversion Experiment

EXAMPLE VII

At a pressure of 3.0 MPa, 81.3 g/hr of methyl 5-formylvalerate, 203 g/hr of ammonia, and 526 g/hr of a 15 wt. % methanol in water mixture was pumped through a tube which was cooled by a water bath so that a constant temperature of 35° C. was maintained in the tube. Almost no back-mixing occurred and the (liquid) residence time was 15 seconds.

The resulting mixture leaving the tube (substep a1) was fed to a continuously stirred tank reactor, a Hastelloy C autoclave of 1 liter liquid volume. The reactor was stirred at 1250 rpm. The pressure was kept at a constant 3 MPa and the temperature at 120° C. To the reactor a net amount of 5 g/hr of hydrogen was fed. The reactor contents included a 5 wt. % ruthenium on $Al_2O_3$ catalyst (Engelhard: ESCAT 44) at a catalyst concentration maintained at 96.0 g/l.

The composition of the effluent (mixture A) of the stirred reactor did not vary significantly during the 22 hours of operation. The average composition of all the products formed in the last 12 hours was 21.5 mol % 6-aminocaproic acid (6ACA), 45.9 mol % 6-aminocaproamide (6ACAM), 27.5 mol % ε-caprolactam (CAP), 2.1 mol % methyl 6-aminocaproate (M6AC) and 3.0 mol. % oligomers.

Mixture A was flashed to 0.1 MPa and continuously fed to the top of a steamstripper column (operated at 0.1 MPa) at a rate of 638 g/hr. Steam was generated in a reboiler of the column. To the column, 212 g/hr of fresh water was also fed. The liquid bottom stream which left the steamstripper (rate 571 g/hr) did not contain any detectable amounts of methanol and ammonia. This aqueous stream consisted of 12.4 wt. % of 6ACA, 6ACAM, M6AC, CAP and oligomers having the same molar contribution as in mixture A.

The aqueous mixture was subsequently fed to the bottom of a continuously operated counter current extraction column. To the top of this column (having 20 theoretical plates) chloroform was fed at a rate of 1.0 l/hr. ε-caprolactam was extracted into the chloroform phase at a more than 99% yield. Pratically all of the 6-aminocaproic acid, 6-aminocaproamide and oligomers remained in the aqueous phase.

This aqueous mixture was subsequently continuously fed to a cyclization reactor, a plugflow reactor (almost no backmixing), at a constant temperature of 320° C. (maintained with the use of an oil bath), a pressure of 12 MPa and at a residence time of 30 minutes, and at a rate of 554 g/hr. The average composition of all the products present in the liquid aqueous stream leaving the cyclization reactor amounted to 7.5 wt. % ε-caprolactam, 1.6 wt. % of 6-aminocaproic acid, 6-aminocaproamide and oligomers.

This aqueous mixture was fed to an extraction comparable to the one described earlier. The stream of chloroform leaving the extraction contained 41.6 g/hr ε-caprolactam. The total yield in this one pass was 92.7% calculated on the molar amount of methyl 5-formylvalerate.

By recycling the aqueous mixture obtained in the extraction to the cyclization reactor, additional production of ε-caprolactam can be obtained. It should also be readily apparent that the extractions here illustrated can be combined in a single unit operation in a commercially operated process.

Accordingly, this invention is defined and limited only by the spirit and scope, including equivalents thereof, of the following claims.
What is claimed is:

1. A process for preparing ε-caprolactam comprising:
  (a) contacting a compound having the formula:

$$O=CH-(CH_2)_4-C(O)-R \qquad (1)$$

wherein R is —OH, —$NH_2$, or —O—R', and
  wherein R' is an alkyl, cycloalkyl, aryl or aralkyl group with 1 to 10 carbon atoms, in an aqueous medium as solvent,
  at an elevated pressure with ammonia and hydrogen in the presence of a hydrogenation catalyst to form a mixture of ε-caprolactam, 6-aminocaproamide, 6-aminocaproate ester, 6-aminocaproic acid and oligomers of said compounds, wherein the yield to ε-caprolactam in (a) is carried to a level of at least 10 molar %, calculated on the initial molar amount of said compound,
  and extracting ε-caprolactam from said aqueous mixture obtained from (a) with an organic extraction agent to form an organic extractant solution of ε-caprolactam and a separate residual aqueous mixture, followed by
  (b) reacting said 6-aminocaproamide, 6-aminocaproate ester, 6-aminocaproic acid and oligomers of said compounds in said residual aqueous mixture to form ε-caprolactam.

2. Process according to claim 1, characterized in that the extraction agent is a chlorinated hydrocarbon solvent.

3. Process according to claims 2, characterized in that the chlorinated hydrocarbon solvent is dichloromethane, chloroform or 1,1,1-trichloroethane.

4. Process according to claim 1, characterized in that the extraction agent is a mono-alcohol having 5–8 carbon atoms.

5. Process according to claim 4, characterized in that the mono-alcohol is a hindered alcohol.

6. Process according to claim 5, characterized in that the alcohol is 4-methyl-2-pentanol.

7. Process according to any one of claims 1–6, characterized in that the formula (1) compound is an alkyl 5-formylvalerate compound, in which R' is a $C_1$–$C_6$ alkyl group, and that said aqueous medium contains between 2 and 20 weight % of HO—R'.

8. Process according to claim 1, characterized in that ε-caprolactam is separated from the aqueous mixture obtained in (b) and from the aqueous mixture obtained in (a) in which the same extraction agents and conditions are applied.

9. Process according to claim 1, wherein the process is carried out continuously.

10. Process according to claim 1, further comprising, after contacting the compound according to formula (1) with ammonia and hydrogen, (a1) reacting the compound according to formula (1) with ammonia under non-hydrogenation conditions and (a2) converting the reaction product obtained in (a1) to ε-caprolactam and 6-aminocaproamide, 6-aminocaproate ester, 6-aminocaproic acid and oligomers of said compounds under hydrogenation conditions in the presence of ammonia.

11. Process according to claim 10, characterized in that the hydrogenation conditions are achieved by converting the reaction product obtained in (a1) in the presence of hydrogen and a ruthenium containing catalyst.

12. Process according to claim 1, characterized in that the concentration of the compound according to formula (1) in (a) is between 10–35 wt. %.

13. Process according to claim 1, characterized in that in (b) is performed in a liquid phase at an ammonia concentration of less than 3 wt. %, a concentration of ε-caprolactam and 6-aminocaproamide, 6-aminocaproate ester, 6-aminocaproic acid and oligomers of said compounds is between 10–35 wt. % and at a temperature between 290 and 350° C.

* * * * *